US00PP18022P2

(12) United States Plant Patent
Klemm

(10) Patent No.: US PP18,022 P2
(45) Date of Patent: Sep. 11, 2007

(54) ***GERANIUM* PLANT NAMED 'KLEP04133'**

(50) Latin Name: *Pelargonium×hortorum*
Varietal Denomination: KLEP04133

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/349,696

(22) Filed: Feb. 7, 2006

(51) Int. Cl.
*A01H 5/00* (2006.01)

(52) U.S. Cl. ..... Plt./328
(58) Field of Classification Search ..... Plt./328
See application file for complete search history.

(56) References Cited

U.S. PATENT DOCUMENTS

PP8,119 P * 1/1993 Stoots ..... Plt./328

OTHER PUBLICATIONS

UPOV ROM GTITM Database, GTI Jouve Retrieval Software 2006/05 Citations for 'KLEP04133'.*

* cited by examiner

*Primary Examiner*—Wendy Haas
(74) *Attorney, Agent, or Firm*—C. A. Whealy

(57) ABSTRACT

A new and distinct cultivar of Zonal *Geranium* plant named 'KLEP04133', characterized by its upright and uniform plant habit; freely branching; early and freely flowering habit; pink-colored flowers arranged in rounded umbels held above the foliage on upright and strong peduncles; and good garden performance.

1 Drawing Sheet

Botanical designation: *Pelargonium×hortorum.*
Cultivar denomination: 'KLEP04133'.

BACKGROUND OF THE INVENTION

The present invention relates to a new and distinct cultivar of Zonal *Geranium* plant, botanically known as *Pelargonium×hortorum,* and hereinafter referred to by the name 'KLEP04133'.

The new Zonal *Geranium* is a product of a planned breeding program conducted by the Inventor in Stuttgart, Germany. The objective of the breeding program was to develop new freely branching Zonal *Geraniums* with upright and uniform plant habit and interesting flower and foliage colors.

The new Zonal *Geranium* originated from a cross-pollination made by the Inventor in July, 2000 of a proprietary selection of *Pelargonium×hortorum* identified as code number U 001, not patented, as the female, or seed, parent with a proprietary selection of *Pelargonium×hortorum* identified as code number U 126, not patented, as the male, or pollen, parent. The cultivar KLEP04133 was discovered and selected by the Inventor as a flowering plant within the progeny from this cross-pollination in a controlled environment in Stuttgart, Germany, in June, 2001.

Asexual reproduction of the new cultivar by terminal cuttings in a controlled environment in Stuttgart, Germany since 2001 has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'KLEP04133'. These characteristics in combination distinguish 'KLEP04133' as a new cultivar and distinguish it from other known Zonal *Geranium* cultivars:

1. Upright and uniform plant habit.
2. Freely branching habit.
3. Early and freely flowering habit.
4. Pink-colored flowers arranged in rounded umbels held above the foliage on upright and strong peduncles.
5. Good garden performance.

Plants of the new Zonal *Geranium* differ from plants of the parent selections primarily in growth habit as plants of the new Zonal *Geranium* are more vigorous than plants of the parent selections.

Plants of the new Zonal *Geranium* can be compared to plants of the cultivar Klesectra, disclosed in U.S. Plant patent application Ser. No. 09/250,008. In side-by-side comparisons conducted in Stuttgart, Germany, plants of the new Zonal *Geranium* differed from plants of the cultivar Klesectra in the following characteristics:

1. Plants of the new Zonal *Geranium* were larger and more vigorous than plants of the cultivar Klesectra.
2. Flower color of plants of the new Zonal *Geranium* was pink whereas flower color of plants of the cultivar Klesectra was red.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of a typical flowering plant of 'KLEP04133' grown in a container.

DETAILED BOTANICAL DESCRIPTION

Plants of the cultivar KLEP04133 have not been observed under all possible environmental conditions. The phenotype may vary somewhat with variations in environment, such as temperature and light intensity, without, however, any variance in genotype.

The aforementioned photograph and following observations and averaged measurements describe plants that were planted in January in containers in Stuttgart, Germany, and grown under commercial practice in a glass-covered greenhouse with day temperatures ranging from 16° C. to 22° C., night temperatures ranging from 12° C. to 16° C. and light levels ranging from 25,000 to 60,000 lux. The photograph and information for the detailed botanical description were taken about 13 weeks after planting rooted young plants. In the following description, color references are made to The Royal Horticultural Society Colour Chart, 1995 Edition, except where general terms of ordinary dictionary significance are used.

Botanical classification: *Pelargonium×hortorum* cultivar KLEP04133.

Parentage:

*Female parent.*—Proprietary selection of *Pelargonium×hortorum* identified as code number U 001, not patented.

*Male parent.*—Proprietary selection of *Pelargonium×hortorum* identified as code number U 126, not patented.

Propagation:

*Type cutting.*—Terminal cuttings.

*Time to initiate roots, summer.*—About 7 days at 22° C.

*Time to initiate roots, winter.*—About 9 days at 20° C.

*Time to produce a rooted young plant, summer.*—About 16 days at 22° C.

*Time to produce a rooted young plant, winter.*—About 18 days at 20° C.

*Root description.*—Fine to thick, fibrous; white in color.

*Rooting habit.*—Moderately dense; freely branching.

Plant description:

*General appearance.*—Upright and uniform plant habit; densely foliated.

*Growth and branching habit.*—Moderately vigorous. Freely branching, about four to five lateral branches develop without pinching, that is, without the removal of terminal apices.

*Plant height* (*to top of flower umbels*).—About 26 cm to 30 cm.

*Plant height* (*to top of foliar plane*).—About 20 cm to 25 cm.

*Plant width.*—About 21 cm to 26 cm.

*Lateral branches.*—Length: About 5 cm to 6 cm. Internode length: About 1.5 cm. Texture: Slightly pubescent. Color: 143C.

*Foliage description.*—Arrangement: Alternate, simple. Length: About 5 cm to 6 cm. Width: About 7 cm to 9 cm. Shape: Rounded to reniform. Apex: Rounded. Base: Lobed, not overlapping. Margin: Crenate, lobed. Venation pattern: Palmate. Texture, upper and lower surfaces: Glabrous; rough. Color: Developing and fully expanded foliage, upper surface: 147A; venation, 147B. Developing and fully expanded foliage, lower surface: 138A; venation, 147D. Zonation pattern: Not observed. Petiole: Length: About 6 cm. Diameter: About 3 mm. Color, upper and lower surfaces: 147D.

Flower description:

*Flower arrangement.*—Pink-colored flowers arranged in rounded hemispherical umbels arising from apical leaf axils. Umbels displayed above the foliage on upright and strong peduncles. Flowers double in form; rounded and cupped. Umbels persistent, flowers not persistent. Flowers not fragrant.

*Quantity of flowers.*—Freely flowering habit; at full flower, plants have about eight developing and open umbels each with about 38 flower buds and flowers.

*Flowering season.*—Year-round under greenhouse conditions. In the garden, flowering is continuous throughout the summer.

*Time to flower.*—Early flowering; plants start flowering about 82 days after planting rooted young plants.

*Flower longevity.*—Flowers last about eight to twelve days on the plant.

*Umbel size.*—Height: About 7 cm. Diameter: About 8 cm.

*Flower size.*—Diameter: About 3.5 cm. Depth (height): About 1 cm.

*Flower buds.*—Length: About 5 mm to 8 mm. Diameter: About 3 mm to 5 mm. Shape: Elliptical. Color: 144C.

*Petals.*—Quantity per flower: About eight to ten. Length: About 1.2 cm to 1.5 cm. Width: About 8 mm to 10 mm. Shape: Ovate. Apex: Rounded. Base: Attenuate. Margin: Entire. Texture, upper and lower surfaces: Smooth, velvety. Color: When opening and fully opened, upper surface: 48C to 48D; towards the apex and towards the base, close to 155A; color does not fade with development; venation, 48C. When opening and fully opened, lower surface: 49A to 49D; towards the apex, close to 157D; towards the base, 155A; venation, 49C.

*Petaloids.*—Quantity per flower: About six to ten. Length: About 2 mm to 6 mm; irregular in size. Width: About 1 mm to 6 mm; irregular in size. Shape: Variable, irregular. Apex: Mostly rounded. Base: Attenuate. Margin: Mostly entire. Texture, upper and lower surfaces: Smooth, velvety. Color: When opening and fully opened, upper surface: 48C; towards the apex and towards the base, close to 155A; color does not fade with development; venation, 48C. When opening and fully opened, lower surface: 49C; towards the apex, close to 157D; towards the base, 155A; venation, 49C.

*Sepals.*—Quantity per flower: Five, arranged in a single whorl. Length: About 5 mm to 8 mm. Width: About 2 mm to 5 mm. Shape: Elliptical. Apex: Acute. Margin: Entire. Texture, upper and lower surfaces: Pubescent, rough. Color, upper and lower surfaces: 144C.

*Peduncles* (*umbel stems*).—Length: About 16 cm. Diameter: About 4 mm to 6 mm. Angle: Erect. Strength: Moderately strong to strong. Texture: Slightly pubescent. Color: 144B.

*Pedicels* (*individual flower stems*).—Length: About 1.2 cm to 1.5 cm. Diameter: About 1.5 mm to 2 mm. Angle: Erect. Strength: Strong. Texture: Slightly pubescent. Color: 144B overlain with 181C.

*Reproductive organs.*—Androecium: Anther quantity per flower: Five. Anther length: About 2.5 mm. Anther shape: Ovate. Anther color: 52D. Pollen amount: Moderate. Pollen color: 33B. Gynoecium:

Pistil quantity per flower: One. Pistil length: About 4 mm to 6 mm. Stigma shape: Five-parted, star-shaped. Stigma color: 57C. Style length: About 3 mm to 4 mm. Style color: 57D. Ovary color: 149D.

*Seeds.*—Seed development has not been observed.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind, and temperatures from about 8° C. to about 30° C. and have good garden performance.

It is claimed:

1. A new and distinct cultivar of Zonal *Geranium* plant named 'KLEP04133', as herein illustrated and described.

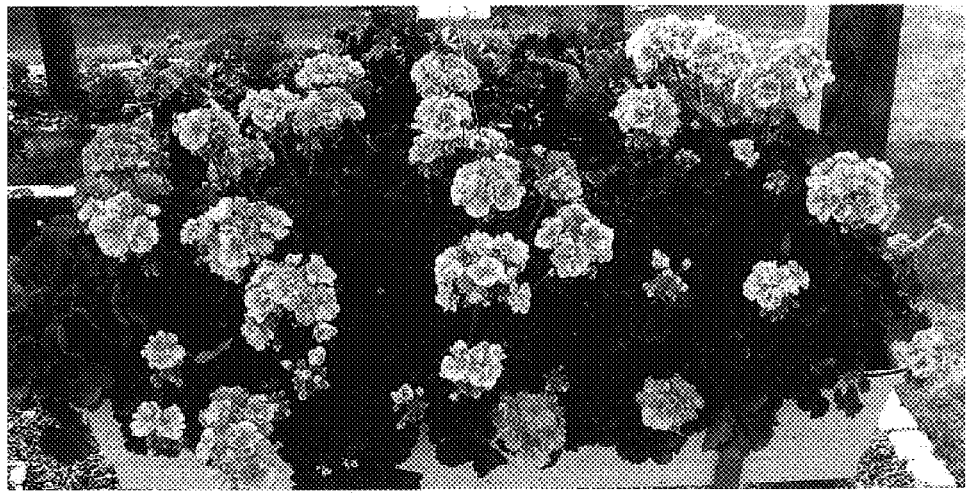

* * * * *